US00RE50202E

(19) United States
(12) Reissued Patent
Alphonse

(10) Patent Number: US RE50,202 E
(45) Date of Reissued Patent: Nov. 12, 2024

(54) NASAL RESPIRATORY ASSEMBLY AND METHODS OF USE

(71) Applicant: Sandra Alphonse, La Mesa, CA (US)

(72) Inventor: Sandra Alphonse, La Mesa, CA (US)

(73) Assignee: Sandra Alphonse, La Mesa, CA (US)

(21) Appl. No.: 17/491,513

(22) Filed: Sep. 30, 2021

Related U.S. Patent Documents

Reissue of:
(64) Patent No.: 10,426,909
Issued: Oct. 1, 2019
Appl. No.: 14/739,898
Filed: Jun. 15, 2015

U.S. Applications:
(63) Continuation of application No. PCT/US2012/072153, filed on Dec. 28, 2012.

(51) Int. Cl.

| | |
|---|---|
| ***A61M 16/06*** | (2006.01) |
| ***A61M 16/08*** | (2006.01) |
| ***A61M 16/10*** | (2006.01) |
| ***A61M 16/12*** | (2006.01) |
| ***A61M 16/16*** | (2006.01) |

(52) U.S. Cl.
CPC ..... *A61M 16/06* (2013.01); *A61M 16/0683* (2013.01); *A61M 16/0875* (2013.01); *A61M 16/1045* (2013.01); *A61M 16/12* (2013.01); *A61M 16/16* (2013.01)

(58) Field of Classification Search
None
See application file for complete search history.

(56) References Cited

U.S. PATENT DOCUMENTS

| | | | |
|---|---|---|---|
| 4,015,598 | A | 4/1977 | Brown |
| 4,951,661 | A | 8/1990 | Sladek |
| 5,311,862 | A | 5/1994 | Blasdell et al. |
| 5,560,354 | A | 10/1996 | Berhon-Jones et al. |

(Continued)

FOREIGN PATENT DOCUMENTS

| | | | |
|---|---|---|---|
| WO | 9943389 | A1 | 9/1999 |
| WO | 2008106716 | A1 | 9/2008 |

(Continued)

OTHER PUBLICATIONS

International Search Report (Form PCT/ISA/210) for International Application No. PCT/US2012/072153 mailed Mar. 29, 2013, 2 pages.

(Continued)

*Primary Examiner* — Glenn K Dawson
(74) *Attorney, Agent, or Firm* — Withrow + Terranova PLLC; Vincent K. Gustafson

(57) ABSTRACT

The present invention is a nasal respiratory assembly and methods of using the same wherein the assembly comprises a mask, a ventilator hose and a strap. The mask has a top surface, a base, an exhaust port having a one-way valve and two rotatable intake ports. The hose has a first end and a second end adapted to be received by the first and second intake ports, and at least a third end to connect to the ventilator. The hose and/or the mask further contain a rotatable medication delivery port to allow treatment delivery in close proximity to the patient.; The rotatable intake ports are located on either side of the mask so that the pressurized air is not delivered directly into the patient's nasal cavities.

13 Claims, 1 Drawing Sheet

(56) References Cited

U.S. PATENT DOCUMENTS

| | | | | |
|---|---|---|---|---|
| 5,701,886 | A | 12/1997 | Ryatt | |
| 6,014,972 | A | 1/2000 | Sladek | |
| 6,135,109 | A | 10/2000 | Blasdell et al. | |
| 7,841,342 | B2 * | 11/2010 | Dhuper | A61M 15/0086 128/200.24 |
| 8,181,650 | B2 * | 5/2012 | Nelson | A61M 16/06 128/203.12 |
| 8,297,285 | B2 * | 10/2012 | Henry | A61M 16/06 128/207.18 |
| 8,910,635 | B2 * | 12/2014 | Pierro | A61M 16/085 128/206.28 |
| 9,044,562 | B2 * | 6/2015 | Dillingham | A61M 16/06 |
| 11,878,124 | B2 * | 1/2024 | Nelson | A62B 18/10 |
| 2002/0117177 | A1 | 8/2002 | Kwok | |
| 2003/0024533 | A1 * | 2/2003 | Sniadach | A61M 16/06 128/206.28 |
| 2003/0150445 | A1 | 8/2003 | Power et al. | |
| 2004/0221850 | A1 | 11/2004 | Ging et al. | |
| 2005/0205096 | A1 * | 9/2005 | Matula, Jr. | A61M 16/0666 128/207.11 |
| 2005/0241644 | A1 | 11/2005 | Gunaratnam et al. | |
| 2006/0081243 | A1 | 4/2006 | McDonald et al. | |
| 2006/0237013 | A1 | 10/2006 | Kwok | |
| 2007/0049841 | A1 * | 3/2007 | Lepel | A61M 11/02 600/534 |
| 2007/0221226 | A1 | 9/2007 | Hansen et al. | |
| 2008/0210242 | A1 * | 9/2008 | Burk | A61M 16/06 128/206.21 |
| 2009/0293881 | A1 * | 12/2009 | Graham | A61M 11/06 128/207.12 |
| 2010/0012129 | A1 | 1/2010 | Kwok et al. | |
| 2012/0216806 | A1 * | 8/2012 | Rookard | A61M 16/06 128/203.29 |
| 2012/0285466 | A1 * | 11/2012 | Pierro | A61M 16/085 128/206.24 |

FOREIGN PATENT DOCUMENTS

| | | | |
|---|---|---|---|
| WO | 2010076683 | A1 | 7/2010 |
| WO | 2014105060 | A1 | 7/2014 |

OTHER PUBLICATIONS

Written Opinion (Form PCT/ISA/237) for International Application No. PCT/US2012/072153 mailed Mar. 29, 2013, 6 pages.

Extended European Search Report for European Patent Application No. 12891299.5 mailed Oct. 17, 2016, 8 pages.

Examination Report No. 1 for Australian Patent Application No. 2012397786 mailed Aug. 8, 2017, 5 pages.

* cited by examiner

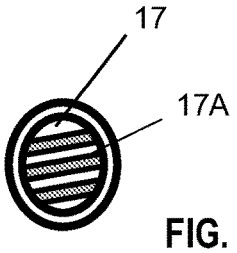
FIG. 2
(NEW)

NASAL RESPIRATORY ASSEMBLY AND METHODS OF USE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

The following application claims the benefit of the filing date of PCT/US2013/29787 filed 8 Mar. 2013 under 35 U.S.C. § 371.

BACKGROUND OF THE INVENTION

1. Field of the Invention

The invention relates generally to a nasal respiratory assembly for delivering a therapeutic treatment, medication and/or pressurized gas to a patient. More specifically, the invention relates to a nasal respiratory assembly comprising a mask and ventilator hose. The mask comprises intake ports, an exhaust port and one or more delivery ports. The nasal respiratory assembly is configured to prevent direct delivery of the therapeutic treatment, medication or pressurized gas into the patient's nasal cavities thereby providing a more comfortable and natural breathing pattern. In an exemplary embodiment, the nasal respiratory assembly configuration allows a medication to be delivered into the pressurized gas flow in close proximity to the patient's nasal cavities.

2. Prior Art

Continuous positive airway pressure or "CPAP" is a common method for ameliorating a variety of breathing disorders including respiratory failure, obstructive sleep apnea and some neuromuscular diseases in adults as well as respiratory distress syndrome and bronchopulmonary dysphasia in infants. CPAP respiratory assemblies typically include a mask connected to a ventilator through a ventilator hose. The ventilator provides a continuous source of pressurized air or other breathable gas using an electrically driven blower that is controlled by a servo and microcontroller unit. During use, the mask is affixed over the nasal passages to create a ventilation chamber and secured to the patient's head by one or more straps. The mask is usually made of a rigid or semi-rigid material and has a face-contacting surface including an intake port, which is aligned with the wearer's nasal cavities. The face-contacting surface is usually prepared of a flexible material that conforms to various facial contours. The straps are adjusted to secure the mask against the face with sufficient force to achieve a relatively gas tight seal.

However, there are numerous disadvantages associated with the use of CPAP ventilators. It has been recognized that the delivery of pressurized gases to the respiratory tract of a patient often results in discomfort, especially when treatment is for an extended period of time.

One primary disadvantage to standard nasal masks used in clinical settings is discomfort due to the speed and force of the pressurized gas being delivered into the nasal cavities. Patients often suffer from dried nasal cavities resulting in nosebleeds and unnatural breathing patterns that can result in coughing or gagging. In some cases, administration of positive pressure ventilation, either mechanical ventilation or non-invasive ventilation, can result in barotrauma (pressure-related injury) leading to a pneumothorax, which is an abnormal collection of air or gas in the pleural space that separates the lung from the chest wall. This condition is very painful and often interferes with normal breathing.

Another disadvantage is the ineffective delivery of medication to the patient when dispensed into the pressurized gas stream from a nebulizer or inhaler. Delivery ports for this type of application are typically set-up proximal to a ventilator. When medication in a nebulized form is dispensed in this fashion, a portion of the medication is lost as it travels through the hose before reaching the patient's nasal cavities. The greater the distance the more the prescribed dosage is diminished. In other cases, the nasal mask is removed from the patient in order to deliver the intended medication using a wall flow meter. Unfortunately, some patients can suffer from poor oxygenation during this process.

Another disadvantage is that the face-contacting portion of the mask can apply excessive pressure to the patient's face resulting in discomfort and skin irritation. Over extended periods of use, these forces can cause facial soreness and/or ulceration.

A variety of mask assemblies have been disclosed. U.S. Pat. No. 5,560,354 discloses an apparatus for use with a ventilator comprising a nose piece to lit over the patient's nose, an intake port on one side of the nosepiece comprising two soft nasal tubes connected to the ventilator, a one-way exhaust port on the other side of the nose piece and a seal about the perimeter for making a gas tight seal against the patient's face. The mask is secured to the head using a headband on which the intake and exhalation port tubes are attached. The disadvantage of this mask assembly is that it provides the pressurized gas flow directly into the nasal cavities, which can make inhalation difficult or result in barotrauma. In addition, neither the mask not the intake port provides an adapter for administering a medication in close proximity to the patient's nasal passages. This makes administration of a proscribed amount of medication difficult. Further, the nosepiece is not directly secured to the patient's face but instead relies on the connection of the flexible intake and exhaust ports to the headband for stability. This design makes it difficult to assure a gas tight seal against the patient's face.

U.S. Pat. No. 7,942,150 discloses a mask assembly for treating a patient comprising a plenum chamber, or mask, adapted to create a seal about the patient's nasal cavities, a support structure for maintaining the mask assembly in place, an exhaust vent, at least one air inlet and a baffle separating the air inlet from the exhaust vent. The disadvantage of this mask assembly is that it provides the pressurized gas flow directly into the nasal cavities. Another disadvantage is the absence of a medication delivery port in close proximity to the patient.

U.S. Pat. No. 6,615,834 discloses a device for delivering gas comprising a mask in communication with a gas supply, at least one outlet vent, a removable filter for filtering the diffusing expired gas and headgear for securing the device to the patient's head. This device suffers from similar disadvantages as those listed above. The orientation of the intake vent on the mask provides pressurized gas directly into the nasal cavities. In addition, there is no delivery port for administering a medication in close proximity to the patients nasal passages.

U.S. Pat. No. 7,913,692 discloses a CPAP mask comprising a shell or body that covers the mouth and nose, a cushion about the perimeter edge, an inlet port and a gas flow generator having a housing for maintaining an impeller to provide gas flow and a motor to drive the impeller. The flow generator is positioned below the base of the nose and delivers pressurized gas directly into the nasal cavities. The disadvantages of this system are similar to those listed above for U.S. Pat. No. 6,615,834. In addition, incorporating the gas flow generator into the mask makes it larger, heavier and more cumbersome to use.

Other patents include: U.S. Pat. No. 8,042,538 which discloses a nasal mask having a rigid body, a single intake port positioned below the nose and directed at the nasal cavities, a cushion about the perimeter edge and headgear comprising a yoke and two straps for securely affixing the mask to the patient's face; U.S. Pat. No. 7,036,508 which discloses a harness assembly adapted to secure a nasal mask to a patient's face comprising a pair of upper and lower straps and a cap portion with D-shaped coupling members for joining the upper and lower straps; and U.S. Pat. No. 8,186,348 which discloses a respiratory mask assembly that comprises a mask having a single intake port and a cushion about its perimeter edge and an adjustable forehead support for maintaining the position of the mask. These three patents demonstrate the necessity for maintaining the mask in position while creating a gas tight seal on the patient's face for efficient and effective treatment. However, the complexity of these devices make them cumbersome to wear and difficult to set-up and maintain their position during use.

Accordingly, there is a need in the field for a nasal respiratory assembly that is easy to use and is able to deliver a breathable medication to a patient both effectively and comfortably.

SUMMARY OF THE INVENTION

The embodiments disclosed below satisfy this need. The following simplified summary is provided in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

In an exemplary embodiment, the present invention is directed to a nasal respiratory assembly for delivering a therapeutic treatment to a patient. The assembly comprises a mask that creates an isolated breathing chamber up against the patient's face and ventilation hose for providing the therapeutic treatment to the mask. The mask has a top surface and a base. It comprises an exhaust port having a one-way valve, at least one rotatable medication delivery port, and a first and second rotatable intake ports positioned on either side of the top surface so that the treatment is not delivered directly into the patient's nasal cavities. The hose has three ends, the first and second ends are adapted to be received by the intake ports and a device that delivers pressurized gas can receive the third end. The hose may further comprise one or more rotatable medication delivery ports positioned proximal to the intake ports so that medication can be delivered in close proximity to the patient.

In another embodiment, the nasal respiratory assembly further comprises a strap for retaining the mask on the patient's face. In this regard, the mask further comprises at least four loop adapters, two on either side, to receive the strap. The strap has U-shaped ends adapted to fit around the patient's ears and be received by the at least four loop adapters. The strap may further comprise one or more connectors for affixing the first and second ends of the ventilation hose to the strap. A number of connectors known to those in the art may be utilized with the present invention and include clips, hooks or Velcro™ straps.

In another embodiment, the rotatable medication delivery port is affixed on the top surface of the mask above the nasal cavities. Alternatively, there may be two rotatable medication delivery ports one on either side of the top surface of the mask and positioned adjacent the first and second intake ports.

In other embodiments, the mask may further comprise a cushion along its base, the exhaust port may comprise a removable filter and the intake ports may further comprise a [direction] *directing* means that deflects pressurized gas from entering the nasal cavities directly. The [direction] *directing* means may be comprised of one or more vents comprising louvers that deflect the pressurized gas to a desired location in the mask.

Other aspects of the invention are found throughout the specification.

BRIEF DESCRIPTION OF THE DRAWINGS

*FIG. 2 is a perspective view of an internal vent with multiple louvers for use with the mask of FIG. 1 according to one embodiment.*

DETAILED DESCRIPTION OF THE INVENTION

Figure 1:
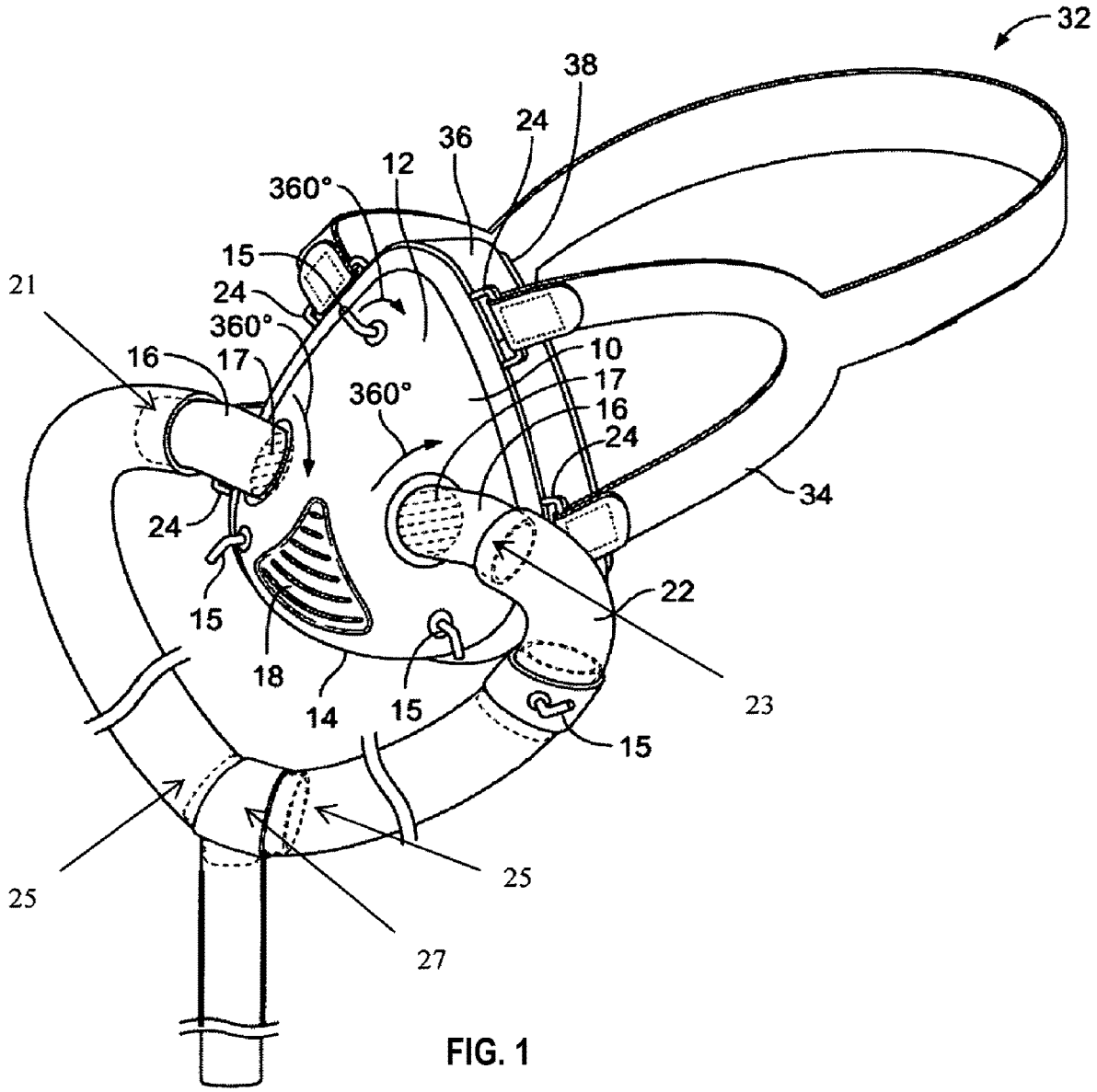
FIG. 1 is a perspective view of an exemplary nasal respiratory mask assembly of the present invention.

Unless defined otherwise, all terms used herein have the same meaning as are commonly understood by one of skill in the art to which this invention belongs. All patents patent applications and publications referred to throughout the disclosure herein are incorporated by reference in their entirety. In the event that there is a plurality of definitions for a term herein, those in this section prevail.

When the terms "one," "a," or "an" are used in this disclosure, they mean "at least one" or "one or more," unless otherwise indicated.

The term "aerosol" as used herein refers to a dispersion of a solid or liquid phase in a gas phase. This dispersion, also termed the discontinuous phase, is comprised of multiple solid or liquid particles. The particle size of the discontinuous phase is typically less than about 100 μm, and in some circumstances considerably less than 100 μm. Both solid and liquid dispersions in a gas phase may be used as pharmaceutical aerosols. Examples of aerosols representing solid particles in a gas phase are those emitted by dry powder inhalers (DPIs). In contrast, pressurized metered-dose inhalers (MDIs) and nebulizers deliver aerosols whose dispersed phase is liquid.

The term "breathable gas" or "gas" as used herein refers to any gas or mixture of gases, which is pharmaceutically acceptable. For example, the gas may simply be air; oxygen enriched air or air combined with a medication, which is common in inhalation therapy using DPIs or MDIs to generate medication aerosols.

The term "rotatable" as used herein, when used in relation to a port such as an intake port or delivery port, refers to a port that is capable of being rotated up to 360 degrees relative to the point of attachment of the port to the mask. As such, in various embodiments, the port can be rotated to 90 degrees, 180 degrees, 270 degrees, 360 degrees or any degrees in between. In addition, this term also encompasses a port having a spherical connector. Spherical connectors increase movement from the typical two-dimensional rotation into three-dimensional rotation.

The term "therapeutic treatment" or "treatment" as used herein refers to administering pressurized air or other breathable gas that may or may not include a medication or medication in aerosol form to provide a therapeutic benefit to a patient.

The invention relates generally to a nasal respiratory assembly for providing a pressurized gas or pressurized gas containing a medication as a therapeutic treatment to a patient. More specifically, the invention relates to a nasal respiratory assembly comprising a mask and a ventilation hose. The mask comprises two intake ports, an exhaust port and one or more delivery ports. The configuration of the nasal respiratory assembly is designed to prevent the delivery of a therapeutic treatment and/or medication directly into the patient's nasal cavities. This design minimizes the risk of epitaxis or barotrauma while providing the patient with a more natural breathing pattern. In exemplary embodiments, the nasal respiratory assembly delivers a medication in close proximity to the patient.

The nasal respiratory assembly of the invention is configured for the delivery of a therapeutic treatment through the nose. In vertebrates the nose is a facial protuberance that houses the nostrils, or nares, which admit and expel air for respiration. In the nostrils of humans, as in most other mammals, are nose hairs that catch airborne particulate contaminants and prevent them from reaching the lungs. Within and behind the nose are the olfactory mucosa and the paranasal sinuses.

The paranasal sinuses consist of four pairs of air-filled cavities or spaces within the bones of the skull and face. They are divided into subgroups which are named according to the bones they lie under: (1) the maxillary sinuses, also called the antra, which are located under the eyes, in the upper jawbone; (2) the frontal sinuses, which lie above the eyes, in the bone of the forehead; (3) the ethmoid sinuses, positioned between the nose and the eyes, backwards into the skull; and (4) the sphenoid sinuses, which are more or less in the center of the skull base. While the primary function of the sinuses is not entirely clear, it appears that they decrease the relative weight of the front of the skull, warm and humidify the inhaled air before it reaches the lungs, increase the resonance of the voice, and perhaps provide a buffer against blows to the face.

During respiration, inhaled air passes through the nasal cavity and sinuses into the pharynx, which is shared with the digestive system, then into the trachea, bronchi and lungs where gas exchange occurs.

The present invention is described more fully hereinafter with reference to the accompanying figures, in which exemplary embodiments of the invention are shown. This invention may, however, be embodied in many different forms and should not be construed as limited to the exemplary embodiments set forth herein.

FIG. 1 shows a perspective view of an exemplary mask assembly 10 according to the invention. The mask assembly includes a mask 10 having a top surface 12 and a base 14. In exemplary embodiments, the mask 10 includes one or more rotatable intake ports 16, which allow one or more hose elements 22 to be connected to the mask 10. In further embodiments, the top surface 12 of mask 10 may further comprise one or more rotatable medication delivery ports 15. In other embodiments the mask 10 includes an exhaust port 18 for releasing exhaled gases from the interior of the mask 10. Additional aspects of the invention include a head strap 32 attached to the mask 10 via one or more loop adapters 24 positioned on either side of the mask 10 to maintain the mask 10 on the patient's [lace] *face* during treatment. Specific features of the nasal respiratory assembly will be discussed in further detail below.

1. Mask

The mask 10 may be constructed in a manner and of materials well known in the art. In certain embodiments, the mask 10 is constructed of a polymeric material and is adapted to fit over a patient's nose to communicate with the patient's respiratory path. In other configurations the mask 10 may be larger in size to fit over the patient's nose and mouth. In various embodiments, the mask 10 is fabricated through a variety of methods known in the art and from non-allergenic materials known to be suitable for contacting a patient's skin. Exemplary materials include thermoplastic resins, polyurethane resins, poly(vinyl chloride), polypropylene, polyethylene, or other plastics. The mask 10 may be prepared using any number of methods known to those skilled in the art including form molding or die casting. In one embodiment, the mask 10 is formed from a clear poly(vinyl chloride) resin or plastic so that a clinician can observe the patient's face while treatments are administered. In this regard, an exemplary poly(vinyl chloride) is VM 1775 NT Clear 0001 (McAllen Company, City of Industry, Calif.). In other aspects, the mask 10 and mask assembly has a relatively slim profile such that the patient's vision is not unduly restricted. In this regard, exemplary embodiments of the invention include triangular and ovoid profiles, however other shapes may also be used.

The mask 10 may be constructed in multiple sizes to fit a variety of different facial contours, and also in multiple configurations, depending on factors such as the method of attachment to the patient's head. Attachment of the mask 10 to the patient's head may be affected in multiple ways, and include providing loop adapters 24 on either side of the mask 10 for receiving a strap 32. Other embodiments may have vents, elbows, pressure ports, or other attachments for items such as a sense tube or oxygen supply port as further options.

In exemplary embodiments, the mask 10 housing includes apertures individually configured as necessary to receive the two intake ports 16, at least one medication delivery port 15 and an exhaust port 18.

2. Ports

In certain embodiments, the mask 10 is fabricated such that the intake ports 16, the one or more medication delivery ports 15 and exhaust port 18 are capable of being in sealed and fluid communication with the apertures located on the mask 10 housing. The intake ports 16 and the one or more medication delivery ports 15 are constructed of a polymeric material that may be identical to the material used to construct the mask 10. Exemplary materials include thermoplastic resins, polyurethane resins, poly(vinyl chloride), polypropylene, polyethylene, or other plastics. The intake ports 16 and the one or more medication delivery ports 15 are of a tubular construction often having a bend of 10 to 45% about the middle. These ports may be prepared using any number of methods known to those skilled in the art including form molding or die casting. The intake port 16 is provided in a diameter that allows the ventilation hose to press fit securely over one end and the medication delivery port 15 is configured to receive medication through the use of MDI or DPI inhalers.

In one configuration, the mask 10 apertures and the ports are provided with snap connectors for easy assembly. To ensure a gas tight seal the apertures or the port snap connectors may further comprise a sealing ring. In certain aspects, the apertures for receiving the intake ports 16 and the one or more delivery ports 15 allow for full rotation of the ports. Rotation may be provided in two- or three-dimensions. In a two-dimensional or 360° rotational aspect, the snap connectors can be provided as a channel and groove configuration allowing for rotation generally in the plane of the upper surface of the mask 10. In a three-dimensional or spherical rotation, the ports may be provided with ball joint connectors and the mask 10 provided with socket apertures that are able to receive the ball joints. In this configuration, the ball joints and socket may be provided in a snap-in configuration. Alternatively, a donut shaped cap that fits over the port and cradles the ball joint may be used. This donut shaped cap may be adhered to the top surface 12 of the mask 10 or be provided with a snap clip that allows it to fasten the ball joint securely in the socket. In addition, these connector configurations provide sufficient friction to minimize unintentional rotation while permitting the intake ports 16 or the one or more delivery ports 15 to be manually rotated about an axis of rotation.

A. Intake Port

In exemplary embodiments, the intake ports 16 are positioned on the mask 10 such that the therapeutic treatment is not delivered directly into a patient's nasal cavities. In this regard, the positioning of the intake ports 16 is such that it reduces the impact of the pressurized gas when it is delivered to the patient through the ventilation hose 22. The result of using a split port design and positioning provides for smoother delivery of the therapeutic treatment to the patient.

In particular aspects, the split port design and positioning as described herein provide a respiratory gas flow rate that is constant and in synchronization with the patient's breathing cycle. More specifically, it maintains the back pressure at a constant level so that the pressure in the patient's respiratory passages is generally at a constant positive differential relative to the exterior room air pressure and does not vary significantly with the patient's inhalation and the exhalation breathing cycle. This design provides the benefit of smoother delivery of a therapeutic treatment to the patient without disrupting the patient's natural breathing pattern. In this configuration, the intake ports 16 direct the pressurized gas towards the sides of the patient's nose, which directs the gas flow to the upper portion of the mask 10 where they collide. This contact reduces the gas flow speed for inhalation as compared to directing the pressurized gas directly into the nasal cavity. As a result, the patient can easily and comfortably inhale the gas intake volumes.

In another embodiment, the intake ports 16 further comprise an internal vent 17 comprising one or more louvers, located proximal to the mask 10 interface, that assist in directing the pressurized gas. *An internal vent 17 with multiple louvers 17A for use with the mask of FIG. 1 is shown in FIG. 2.* In this configuration, there are one or more planar surfaces or louvers, provided within the internal diameter of the intake port angled at a desired degree. These planar surfaces are of a generally consistent width stretching from one side of the intake port to the other. They may be provided in an adjustable or fixed position configuration. If they are adjustable for example, the louver angle can be adjusted from 0 to 90 degrees from the horizontal, with 0 degrees providing unobstructed flow of the pressurized gas into the mask 10 and 90 degrees acting to close the intake port 16. Alternatively, the intake port 16 may further comprise a rotatable housing containing the louvers in a fixed position. In this configuration, the vent housing 17 is exposed on the exterior of the intake port 16 proximal to the mask 10 interface. The vent 17 may be adjusted by turning the housing in either direction. If the louvers are fixed, the angle can be set at a range from 10 to 45 degrees from the horizontal. Since the vent 17 is provided within the internal diameter of the intake port 16, the rotation of the port will also adjust the direction of the pressurized gas flow.

In another configuration, the vent 17 that control the pressurized gas flow through the intake port 16 is provided in the intake port aperture of the mask 10. While in this configuration the vent 17 can be rotatable or fixed, they will not be subject to adjustment by the rotation of the intake port 16. In a rotatable configuration for example, the mask 10 will further comprise one or more vent housings 17 adapted to be received in the intake port apertures. The vent housing 17 may be provided with an adjustment lever that projects from the top surface 12 of the mask 10 for easy access. In a fixed configuration for example, the vent housing 17 merely fits into the intake port aperture before the intake port 16 is installed.

B. Medication Delivery Port

In another embodiment, the one or more medication delivery ports 15 may be positioned on the surface 12 of the mask 10 to allow for easy access and ease of use when dispensing an aerosol dosage of a medication to the patient. The delivery ports 15 are constructed of a polymeric material that may be identical to the material used to construct the mask 10. Exemplary materials include thermoplastic resins, polyurethane resins, poly(vinyl chloride), polypropylene, polyethylene, or other plastics. The delivery port 15 may be prepared using any number of methods known to those skilled in the art including form molding or die casting.

In one configuration, a single medication delivery port 15 is positioned on the top surface 12 of the mask 10 centrally located above the nose. Alternatively, two medication delivery ports 15 may be provided one on either side of the mask 10 adjacent to the intake ports 16 for easy access from either side of the patient. In another configuration, the medication delivery port 15 is provided on the ventilation hose 22 in close proximity to the patient. One advantage provided by a rotatable port 15 is added flexibility when connecting to a metered dose inhaler.

In another configuration, the medication delivery port 15 is provided in-line and in fluid connection with the ventilation hose 22 and in close proximity to the patient. The medication delivery port 15 may be comprised of a tubular body having an adapter on either end for placement in-line on the ventilator hose 22, a rotatable ring that is affixed about the tubular body that allows 360 degree rotation about the longitudinal axis of the ventilation hose 22 and a connector on the rotatable ring for receiving the MDI or DPI. The connector may be affixed to the rotatable ring such that the connector is rotatable and in fluid connection with the rotatable ring. The rotatable connector may be a snap connector having a channel and groove configuration.

In another aspect, the delivery port 15 is placed adjacent to the intake port 16. One advantage of a delivery port 15 is that the patient will not have to be taken off of a ventilator or nebulizer in order to receive medication, thereby avoiding the risk of poor oxygenation. In some aspects, the delivery port 15 can be configured to receive a MDI or any other suitable device to deliver the desired medication to the patient. Examples of such devices include, but not are limited to, DPIs and nebulizers. It shall be understood that any pressurized metered dose inhaler as known in the art may be used.

In certain embodiments, an aerosol delivery device can be connected to the mask 10 on the delivery port 15, which can be rotated to different positions depending on the mode of use and aerosol drug delivery method. For example, if a nebulizer is to be used to generate the mist or aerosol, the aerosol delivery device can be orientated to be substantially vertically disposed relative to the mask 10. If an MDI is to be used as the aerosol drug delivery device, then the delivery port 15 can be rotated so that the MDI is in a substantially horizontal position. Unlike a nebulizer, an MDI will not function correctly when the aerosol chamber is in the vertical position. It must be held horizontally to engage with the aerosol chamber. In this regard, the rotation of the delivery port 15 provides improved accessibility and optimum position for using either a nebulizer or an MDI to ensure correct dosage is administered. In other aspects, the rotational movement of the delivery port 15 provides ease of access and eliminates the necessity for extra accessories or adapters to accommodate either the nebulizer or the MDI, thus providing an integrated solution.

C. Exhaust Port

In another embodiment, the mask 10 includes an exhaust port 18 that allows exhaled gas to exit. The exhaust port 18 is constructed of a polymeric material that may be identical to the material used to construct the mask 10. Exemplary materials include thermoplastic resins, polyurethane resins, poly(vinyl chloride), polypropylene, polyethylene, or other plastics. The exhaust port may be prepared using any number of methods known to those skilled in the art including form molding or die casting. In one embodiment, an aperture is formed in the mask 10 for receiving the exhaust port 18.

In another aspect, the exhaust port 18 comprises a one-way valve to prevent air from the surrounding environment entering the mask 10 through the exhaust port 18 and to allow exhaled aerosols within the mask 10 to be expelled into the environment. The one-way valve may be provided in a variety of configurations known to those skilled in the art. These include a diaphragm check valve, a ball check valve, a swing check valve or tilt check valve, an in-line check valve or a duckbill check valve. If the one-way valve is a diaphragm check valve for example, the valve comprises a flexing rubber diaphragm positioned to create a normally closed valve. When the pressure on the interior of the mask 10 is greater than the pressure on the exterior by a certain amount, the pressure differential, the check valve will open allowing gas flow into the environment. Once positive pressure stops, the diaphragm automatically flexes back to its original closed position.

In another embodiment, the exhaust port 18 further comprises a removable filter so that aerosols and/or medication in the mask 10 are not expelled into the surrounding environment. The filter can be made of a variety of materials known in the art and used as a barrier to prevent the transmission of aerosols into the environment. Materials such as cotton or non-woven polyester are commonly used. The filters may be retained within the exhaust port 18 by a variety of methods. For example, the exhaust port 18 may have a cavity with an inwardly projecting perimeter edge for receiving a filter. When the filter is press fit into the cavity, the inwardly projecting perimeter edge covers the edges of the filter maintaining the filter in place. Alternatively, the exhaust port 18 may have a hinged lid that can be opened and closed upon the filter locking it in the exhaust port. The lid is configured to allow exhaled gas to pass though the filter and into the environment. For example, the lid may appear as an open frame, such that when closed, the perimeter edge of the frame maintains the filter in place. Alternatively, the lid may have vertical or horizontal struts giving the appearance of a grate that maintains the filter in place when closed.

3. Hose

In addition to the nasal respiratory assembly further comprises a hose element 22 adapted to be received by the intake ports 16. In certain embodiments, the hose element 22 is fabricated from any suitable material as is known in the art. Exemplary materials include polyurethane and poly (vinyl chloride).

The hose element 22, also referred to as the ventilation hose 22, may be connected to the one or more intake ports 16 by any connecting means as are known in the art. Typically, these connections provide an intake port 16 exterior diameter slightly larger than the interior diameter of the hose 22 end. This provides a secure and gas tight seal when the hose 22 is press fit onto the intake port 16. In an exemplary embodiment, the ventilation hose 22 is provided with three ends, a first end 21 and a second end 23 adapted to be received by said first and second intake ports, and at least a third end 25, using a "Y" or "U"-shaped coupling 27, as shown in FIG. 1. In this configuration, the hose elements 22 are received by the intake ports 16 such that the intake ports 16 are connected in fluid communication to the hose element 22 creating a relatively gas tight seal. The Y or U-shaped connectors 27 are constructed of a polymeric material that may be identical to the material used to construct the mask 10. Exemplary materials include thermoplastic resins, polyurethane resins, poly(vinyl chloride), polypropylene, polyethylene, or other plastics. These connectors may be prepared using any number of methods known to those skilled in the art including form molding or die casting. The length of the hose connected to the intake ports to the Y or U-shaped connector 27 are generally the same length and shorter than the hose 22 portion connecting the Y or U-shaped connector 27 to the ventilator. The length of the hose 22 from the intake ports 16 to the Y or U-shaped connector 27 may range from six inches to thirty-six inches. The length of the remaining hose 22 will depend on the distance between the user and the ventilator or the device providing the pressurized gas.

In another embodiment, the hose element 22 is configured to receive a one or more medication delivery ports 15. The delivery port 15 may be comprised of a tubular body having an adapter on either end for placement in-line on the ventilator hose 22, a rotatable ring that is affixed about the tubular body that allows 360 degree rotation about the longitudinal axis of the ventilation hose 22 and a connector on the rotatable ring for receiving the MDI or DPI. The connector may be affixed to the rotatable ring such the connector is rotatable and in fluid connection with the rotatable ring. The rotatable connector may be a snap connector having a channel and groove configuration. In one aspect, a delivery port 15 may be connected to the hose element 22 at a position proximal to a patient. In this regard, the potential loss of medication due to impacting and adhering to the ventilation hose 22 is minimized as compared to the general practice of placing the port at greater distances from the patient.

In another embodiment, the hose element 22 may further comprise one or more respiratory gas humidifiers that assist in preventing complications due to drying of the respiratory mucosa, such as mucus plugging and endotracheal tube occlusion during respiratory therapy. There are a variety of methods of providing both moisture and heat to pressurized gas during treatment. These include active respiratory gas humidifiers, evaporators, bubble humidifiers and heat moisture exchangers (HMEs). An active respiratory gas humidifier ensures that patients on mechanical ventilation are supplied with optimally conditioned respiratory gas. In active humidifying processes, moisture and heat is input to respiratory gas by an electrically powered humidifier. Performance data and safety-related requirements for active respiratory gas humidifiers are specified by the standard ISO 8185. According to that standard, the minimum water content of inspired respiratory gas is ca. 33 mg/dm$^3$ and the maximum respiratory gas temperature is ca. 42° C.

Evaporators enrich the inspired respiratory gas with water vapor. In a throughflow evaporator, the inspiration flow is fed through a warmed water bath; in a surface evaporator however, the inspiration flow is guided along the surface of the heated water. Consequently, a surface evaporator transports only water vapor and no water droplets to the patient. The advantage is that water vapor is free of germs thereby reducing the chance of infection.

Bubble humidifiers work similarly as compared to evaporators, but instead guide inspiration flow through a heated water capillary system as opposed to a water bath.

HMEs, unlike the other respiratory humidifiers, are independent from any external energy source or external water supply. They function as heat and moisture exchangers and are placed like an artificial nose between a tube and Y piece. HMEs re-supply heat and moisture withdrawn from expirations to the inspired gas during the following inspiration. The benefit of using an HME is the elimination of additional equipment needed to humidify or heat the pressurized gas. A variety of HMEs that are available commercially may be utilized with the present invention.

4. Strap

In various embodiments, the mask 10 includes one or more loop adapters 24 for affixing a flexible elastic head strap 32. In one aspect, the mask 10 has one loop adapter 24 on each side for attaching a head strap 32. In certain aspects, the mask 10 is deployed over a patient's nose such that the head strap 32 is looped behind the patient's ears to secure the mask 10 in place.

A disadvantage associated with the use of a single strap positioned above the ears of the patient is that such a configuration cannot effectively balance movements generated by an oro-nasal interface. This imbalance can be corrected by using a strap having U-shaped ends 34 adapted to go around a patient's ears, over and under, which stabilizes the mask 10 and provides added comfort. In this configuration, the mask 10 has four loop adapters 24 configured to receive "U" shaped ends of an exemplary head strap 32.

In certain aspects, the strap ends 34 will be secured at the loop adapters 24 and the head strap 32 will go around the back of the patient's head. In one embodiment, the mask assembly includes a head strap 32 made up of a left and a right front ends 34 preferably being mirror images of each other. In certain aspects, the left and right ends 34 are formed in one piece or otherwise interconnected together by mechanical fastening or the like. In another aspect, the left and right front ends 34 are in the general form of a "U" which allows for one portion of the front end 34 to sit above the patient's ear and the remaining portion of the front end 34 to sit below the patient's ear.

In various embodiments, the loop adapters 24 may be permanently or detachably affixed to the mask 10. In various embodiments, the head strap 32 may be made of a variety of elastic materials known to those skilled in the art for retaining a mask 10 on the face of a user. These materials may be natural or synthetic and may be non-allergenic. The head strap 32 may be made from a rubber or a laminated fabric or foam, such as neoprene. One commercially available material is "Breath-O-Prene"™, manufactured by AccuMed, Inc. (Lawrenceville, N.J.). In this regard, it should be understood that the strap 32 may be constructed of virtually any material (elastic or inelastic) that will rapidly respond to and resist movement of the mask 10 on the patient's face.

5. Cushion

In another embodiment, the mask 10 may comprise a cushion 36 attached along the perimeter of the base 14 of the mask 10. The mask cushion 36 is designed to provide a comfortable fit and relatively gas tight seal while minimizing irritation with pressure sensitive regions on the face. In one embodiment, the mask cushion 36, which can range from 3.0 mm to 25.0 mm in thickness and may be permanently or detachably affixed to the mask 10. If the cushion 36 is permanently affixed it may be attached by a variety of methods including co-molding or over-molding techniques, adhesive and/or mechanical fastening means.

In various embodiments, the mask cushion 36 includes a face contacting layer 38 formed from a gel-like material that is hypo-allergenic or non-allergenic and latex-free. A variety of materials may be used to achieve the desired seal and comfort; such as but not limited to, elastomer, silicone, polyurethane, thermoplastic elastomers, foamed elastomers and/or composites. In certain aspects, the gel-like material may be mildly adhesive-like, slightly adhering to the face, reducing or eliminating movement of the mask 10 on the face. The face-contacting layer 38 acts to promote breathability and conformation of the mask 10 to the skin while reducing the incidence of pressure ulcers from forming on the bridge of the nose and other pressure sensitive areas of the face. In use, the face-contacting layer 38 snugly seals about the lower portion of the nasal bridge, along either side of the nose and across the upper lip.

Another advantage of the mask cushion 36 and/or face-contacting layer 38 is that its flexibility allows the cushion to contour to a variety of facial features creating an effective seal on the face of most, if not all, patients. For example, the flexibility of the mask cushion 36 allows a gas tight seal to be maintained during movement when the patient is asleep. As such, the various elements of the mask cushion 36 and the head strap 32 cooperate to ensure maintenance of a seal around the nasal area of the patient by minimizing external forces on the mask 10.

In exemplary embodiments, the face-contacting layer 38 is elastomeric having a width of from 3.0 mm to about 40.0 mm and a thickness of 0.1 mm to about 5.0 mm.

6. Uses

In exemplary embodiments, pressurized gas is supplied to the mask through the ventilation hose connected between the hose element and a ventilator or pressurized gas supply unit (not shown). In some embodiments, the pressured gas supply unit comprises an inhaler, atomizer or nebulizer, which is of the ultrasonic, jet or electro-hydrodynamic type, an MDI and/or a DPI.

In other embodiments, either a commercially available or specially designed MDI may be used in conjunction with the nasal respiratory assembly of the invention. In one aspect, the MDI is connected to the delivery port to allow delivery of the medication to the patient. Once the MDI has been actuated, a metered dose of a medication enters through the delivery port, travels through the hose element to the mask where it is inhaled by the patient. In another aspect the MDI is connected to the delivery port on the mask. When the MDI has been actuated, a metered dose of a medication is delivered directly to the mask where it is inhaled by the patient.

In some aspects, the gas supply unit includes a gas pumping component which may include a compressor (gas compressor), diaphragm pump, piston pump, turbine, gas supply connector, nebulizer or ventilator. The gas used may simply be compressed air, which is most common in inhalation therapy using nebulizers as aerosol generators. Alternatively, other gases and gas mixtures, such as air enriched with oxygen or mixtures of helium, nitrogen, carbon, inert gases, water and oxygen may be used.

In some embodiments, the medication is a respiratory gas that has been conditioned prior to delivery of the same to the patient. In certain embodiments, a humidifier is provided for conditioning the respiratory gas prior to delivery to the patient. In this regard, the respiratory gas is typically warmed and humidified to minimize and/or avoid respiratory irritation from temperature differences or dryness that can result in nosebleeds or epitaxis. In various embodiments, the respiratory gas is heated to temperatures acceptable to comfortable respiration. In other embodiments, the gas is humidified and delivered at a relative humidity of between 50 and 100 percent, and in other embodiments, of between 70 and 80 percent. In certain embodiments, the respiratory gas is heated and humidified.

In other embodiments, the nasal respiratory assembly further comprises an optionally attached Heat & Moisture Exchange (HME) adapter to provide physiological conditioning of inspired gas during mechanical ventilation.

With regard to the medication that is delivered to the patient, the breathing gas shall be understood to include virtually all such gases used for therapeutic purposes. Such gases may include, for example, oxygen-enriched air.

In one embodiment, the medication is a pharmaceutical aerosol for the delivery of an active compound. An active compound is a natural, biotechnology-derived or synthetic compound or mixture of compounds useful for the diagnosis, prevention, management or treatment of a disease, condition, or symptom of an animal, in particular a human. Other terms that may be used as synonyms of active compound include, for example, active ingredient, active pharmaceutical ingredient, drug substance, drug and the like.

In other embodiments, the breathing gas may be any suitable therapeutic drug substance which is useful for the prevention, management, or treatment of any disease, symptom, or condition affecting the nose, the sinuses and/or the osteomeatal complex, such as acute and chronic sinusitis, such as allergic sinusitis, seasonal sinusitis, bacterial sinusitis, fungal sinusitis, viral sinusitis, frontal sinusitis, maxillary sinusitis, sphenoid sinusitis, ethmoid sinusitis, vacuum sinusitis; acute and chronic rhinitis, such as allergic rhinitis, seasonal rhinitis, bacterial rhinitis, fungal rhinitis, viral rhinitis, atrophic rhinitis, vasomotor rhinitis; any combination of rhinitis and sinusitis (i.e. rhinosinusitis); nasal polyps, nasal furuncles, epistaxis, wounds of the nasal or sinunasal mucosa, such as after injury or surgery; and dry nose syndrome; nasal or sinunasal conditions caused by lower respiratory tract diseases such as inflammation, affection, whooping cough, tuberculosis, allergy, bronchitis, asthma, chronic obstructive pulmonary disease and cystic fibrosis, bronchial ecstasies, lung obstruction, lung transplantations; nasal or sinunasal conditions caused by ear diseases such as inflammation of the middle ear (otitis media), inner ear, external ear, ear canal and eustachian tube. The nasal respiratory assembly of the invention allows for a highly efficient deposition of the active compound in the nasal cavities, the paranasal sinuses and/or the respiratory system. Thus, it may be advantageously used for the prevention, management, or treatment of the above diseases, symptoms or conditions.

Among the active compounds which may be useful for serving one of these purposes are, for example, substances selected from the group consisting of anti-inflammatory compounds, glucocorticoids, anti-allergic drugs, antioxidants, vitamins, leucotriene antagonists, anti-infective agents, antibiotics, antifungals, antivirals, mucolytics, decongestants, antiseptics, cytostatics, immunomodulators, vaccines, wound healing agents, local anesthetics, oligonucleotides, peptides, proteins and plant extracts.

Examples of potentially useful anti-inflammatory compounds are glucocorticoids and non-steroidal anti-inflammatory agents such as betamethasone, beclomethasone, budesonide, ciclesonide, dexamethasone, desoxymethasone, fluoconolone acetonide, flucinonide, flunisolide, fluticasone, icomethasone, rofleponide, triamcinolone acetonide, fluocortin butyl, hydrocortisone, hydroxycortisone-17-butyrate, prednicarbate, 6-methylprednisolone aceponate, mometasone furoate, dehydroepiandrosterone-sulfate, elastane, prostaglandin, leukotriene, bradykinin antagonists, non-steroidal anti-inflammatory drugs, such as ibuprofen including any pharmaceutically acceptable salts, esters, isomers, stereoisomers, diastercomers, epimers, solvates or other hydrates, prodrugs, derivatives, or any other chemical or physical forms of active compounds comprising the respective active moieties.

Examples of anti-infective agents, whose class or therapeutic category is herein understood as comprising compounds which are effective against bacterial, fungal, and viral infections, i.e., encompassing the classes of antimicrobials, antibiotics, antifungals, antiseptics, and antivirals, are:

Penicillins, including benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), and amiidine penicillins (mecillinam);

Cephalosporins, including cefazolins (cefazolin, cefazedone); cefuroximes (cerufoxim, cefamdole, cefotiam), cefoxitins (cefoxitin, cefotetan, flomoxel), cefotaximes (cefotaxime, ceftriaxone, ceftizoxime, cefmenoxime), celtazidimes (ceftazidime, cefpirome, cefepime), cefalexins (cefalexin, cefaclor, cefadroxil, ceracline, loracarbef, cefprozil), and cefiximes (cefixime, cefpodoxim proxetile, cefuroxime axetil, cefradine, pivoxil, cefotiam hexetil), loracarbef, cefepim, clavulanic acid/amoxicillin, Ceftobiprole;

Synergists, including beta-lactamase inhibitors, such as clavulanic acid, sulbactam, and tazobactam;

Carbapenems, including imipenem, cilastin, meropenem, doripenem, tebipcncm, ertapenem, ritipenam, and biapenem;

Monobactams, including aztreonam;

Aminoglycosides, such as apramycin, gentamicin, amikacin, isepamicin, arbekacin, tobramycin, netilmicin, spectinomycin, streptomycin, capreomycin, neomycin, paromoycin, and kanamycin;

Macrolides, including erythromycin, clarythromycin, roxithromycin, azithromycin, dithromycin, josamycin, spiramycin and telithromycin;

Gyrase inhibitors or fluroquinolones, including ciprofloxacin, gatifloxacin, norfloxacin, ofloxacin, levofloxacin, perfloxacin, lomefloxacin, fleroxacin, garenoxacin, clinafloxacin, sitafloxacin, prulifloxacin, olamufloxacin, caderofloxacin, gemifloxacin, balofloxacin, trovafloxacin, and moxifloxacin;

Tetracycline, including tetracyclin, oxytetracyclin, rolitetracyclin, minocyclin, doxycycline, tigecycline and aminocycline;

Glycopeptides, including vancomycin, teicoplanin, ristocetin, avoparcin, oritavancin, ramoplanin, and peptide 4; polypeptides, including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin;

Sulfonamides, including sulfadiazine, sulfamethoxazole, sulfalene, co-trimmoxazole, co-trimetrol, co-trimoxazine, and co-tetraxazine;

Azoles, including clotrimazole, oxiconazole, miconazole, ketoconazole, itraconazole, fluconazole, metronidazole, tinidazole, bifonazol, ravuconazol, posaconazol, voriconazole, and ornidazole and other antifungals including flucytosin, griseofluvin, tonoftal, naftitin, terbinatin, amorolfin, ciclopiroxolamin, echinocandins, such as micafungin, caspotmuin, aniclula.

Nitrofurans, including nitrofurantoin and nitrofuranzone;

Polyenes, including amphotericin B, natamycin, nystatin, flucocytosine;

Other antibiotics, including tithromycin, lincomycin, clindamycin, oxazolindiones (linzezolids), ranbezolid, streptogramine A+B, pristinamycin aA+B, Virginiamycin A+B, dalfopristin/qiunupristin (Synercid), chloramphenicol, ethambutol, pyrazinamid, terizidon, dapson, prothionamid, fosfomycin, fucidinic acid, rifampicin, isoniazid, cycloserine, terizidone, ansamycin, lysostaphin, iclaprim, mirocin B17, clerocidin, filgrastim, and pentamidine;

Antivirals, including aciclovir, ganciclovir, birivudin, valaciclovir, zidovudine, didanosin, thiacytidin, stavudin, lamivudin, zalcitabin, ribavirin, ncvirapirin, delaviridin, trifluridin, ritonavir, saquinavir, indinavir, foscarnet, amantadin, podophyllotoxin, vidarabine, tromantadine, and proteinase inhibitors;

Antiseptics, including acridine derivatives, iodine-povidone, benzoates, rivanol, chlorhexidine, quarternary ammonium compounds, cetrimides, biphenylol, clorofene, and octenidine;

Plant extracts or ingredients, such as plant extracts from chamomile, hamamelis, echinacea, calendula, thymian, papain, pelargonium, pine trees, essential oils, myrtol, limonen, cineole, thymol, mentol, camphor, tannin, alpha-hederin, bisabolol, lycopodin, vitapherole;

Wound healing compounds including dexpantenol, allantoin, vitamins, hyaluronic acid, alpha-antitrypsin, anorganic and organic zinc salts/compounds, salts of bismuth and selen;

Interferons (alpha, beta, gamma), tumor necrosis factors, cytokines, interleukines;

Immunmodulators including methotrexat, azathioprine, cyclosporine, tacrolimus, sirolimus, rapamycin, mofetil; mofetil-mycophenolate;

Cytostatics and metastasis inhibitors;

Alkylants, such as nimustine, melphanlane, carmustine, lomustine, cyclophosphosphamide, ifosfamide, trofosfamide, chlorambucil, busulfane, treosulfane, prednimustine, thiotepa;

Antimetabolites, e.g. cytarabine, fluorouracil, methotrexate, mercaptopurine, tioguanine;

Alkaloids, such as vinblastine, vincristine, vindesine; antibiotics, such as alcarubicine, bleomycine, dactinomycine, daunorubicine, doxorubicins, epirubicine, idarubicine, mitomycine, plicamycine;

Complexes of transition group elements (e.g. Ti, Zr, V, Nb, Ta, Mo, W, Pt) such as carboplatinum, cis-platinum and metallocene compounds such as titanocendichloride;

Amsacrine, dacarbazine, estramustine, etoposide, beraprost, hydroxycarbamide, mitoxanthrone, procarbazine, temiposide; paclitaxel, iressa, zactima, poly-ADP-ribose-polymerase (PRAP) enzyme inhibitors, banoxantrone, gemcitabine, pemetrexed, bevaeizumab and ranibizumab.

Examples of potentially useful mucolytics are DNase, P2Y2-agonists (denufosol), drugs affecting chloride and sodium permeation, such as N-(3,5-Diamino-6-chloropyrazine-2-carbony)-N'-{4-[4-(2,3-dihydroxypropoxy)-phenyl] butyl}guanidine methanesulfonate (PARION 552-02), heparinoids, guaifenesin, acetylcysteine, carbocysteine, ambroxol, bromhexine, tyloxapol, lecithins, myrtol and recombinant surfactant proteins.

Examples of potentially useful vasoconstrictors and decongestants that may be useful to reduce the swelling of the mucosa are phenylephrine, naphazoline, tramazoline, tetryzoline, oxymetazoline, fenoxazoline, xylometazoline, epinephrine, isoprenaline, hexoprenaline and ephedrine.

Examples of potentially useful local anaesthetic agents include benzocaine, tetracaine, procaine, lidocaine and bupivacaine.

Examples of potentially useful antiallergic agents include the aforementioned glucocorticoids, cromolyn sodium, nedocromil, cetrizin, loratidin, montelukast, roflumilast, ziluton, omalizumab, heparinoids and other antihistamine, including azelastine, cetirizin, desloratadin, ebastin, fexofenadin, levocetirizin and loratadin.

Antisense oligonucleotides are short synthetic strands of DNA (or analogs) that are complementary or antisense to a target sequence (DNA, RNA) designed to halt a biological event, such as transcription, translation or splicing. The resulting inhibition of gene expression makes oligonucleotides dependent on their composition useful for the treatment of many diseases and various compounds are currently clinically evaluated, such as ALN-RSVOI to treat the respiratory syncytical virus by, AVE-7279 to treat asthma and allergies, TPI-ASM8 to treat allergic asthma, 1018-ISS to treat cancer.

Examples of potentially useful peptides and proteins include antibodies against toxins produced by microorganisms, antimicrobial peptides such as cecropins, defensins, thionins and cathelicidins.

For any of these and other explicitly mentioned examples of drug substances that are potentially useful for carrying out the invention, the compound names given herein should be understood as also referring to any pharmaceutically acceptable salts, solvates or other hydrates, prodrugs, isomers, or any other chemical or physical forms of the respective compounds comprising the respective active moieties.

Thus, it can be seen that an advantageous construction of a nasal respiratory assembly may be had according to the invention. The nasal respiratory assembly as described provides for ease of use and efficacious delivery of medication to a patient while minimizing discomfort to the patient.

The disclosure set forth above is provided to give those of ordinary skill in the an complete disclosure and description of how to make and use embodiments of the compositions and methods of the present invention, and are not intended to limit the scope of what the inventors regard as their invention. Modifications of the above-described modes (for carrying out the invention that are obvious to persons of skill in the art) are intended to be within the scope of the following claims. All publications, patents, and patent applications cited in this specification are incorporated herein by reference in their entirety as if each such publication patent or patent application were specifically and individually indicated to be incorporated herein by reference.

What is claimed is:

1. A nasal respiratory assembly for delivering a therapeutic treatment to a patient comprising:

a) a mask having a top surface and a base, wherein said mask is configured with an exhaust port [having a one-way valve] positioned on said top surface;

b) a first rotatable intake port and a second rotatable intake port positioned on either side of said top surface, wherein *each of* said first and said second rotatable intake ports further comprises a directing means that directs pressurized gas *away* from entering said patient's nasal cavities directly, and wherein said directing means is one or more louvered vents;

c) a hose having a first end and a second end adapted to be received by said first and second intake ports, and at least a third end; and d) [a] *at least one* rotatable medication delivery port provided on said hose and positioned proximal to at least one of said intake ports; and wherein said therapeutic treatment is not delivered directly into the patient's nasal cavities.

[2. The nasal respiratory assembly according to claim 1, wherein said rotatable medication delivery port is affixed on said top surface of said mask.]

3. The nasal respiratory assembly according to claim 1, wherein said first and said second rotatable intake ports are positioned one on either side of said mask such that said therapeutic treatment is received above and on either side of said patient's nasal cavities.

4. The nasal respiratory assembly according to claim 1, wherein said exhaust port is [positioned on said top surface of said mask] *configured to be placed* below [said] *the patient's* nasal cavities *when said mask is worn by the patient*.

[5. The nasal respiratory assembly according to claim 1, wherein said rotatable medication delivery port is provided on said top surface of said mask.]

6. The nasal respiratory assembly according to claim 1, wherein said [nasal respiratory assembly further] *at least one rotatable medication delivery port* comprises [two] *first and second* rotatable medication delivery ports [one on either side of said top surface adjacent] *proximal* to said first and said second intake ports, *respectively*.

[7. The nasal respiratory assembly according to claim 1, wherein said exhaust port further comprises a removable filter.]

8. The nasal respiratory assembly according to claim 1, further comprising a strap and at least four loop adapters two on either side of said mask, wherein said strap has U-shaped ends adapted to be received by said at least four loop adapters for retaining said mask on the face of said patient.

[9. The nasal respiratory assembly according to claim 8, wherein said strap further comprises a connector for affixing said first and second ends of said hose to said strap.]

[10. The nasal respiratory assembly according to claim 9, wherein said connector is one or more clips, hooks or Velcro™ strips.]

11. A method for administering respiratory therapy to a patient comprising the steps of:

affixing, *to a patient,* a nasal respiratory assembly comprising:

a) a mask having a top surface and a base, wherein said mask is configured with an exhaust port [having a one-way valve] positioned on said top surface;

b) a first rotatable intake port and a second rotatable intake port positioned on either side of said top surface, wherein *each of* said first and said second rotatable intake ports further comprises a directing means that directs pressurized gas *away* from entering said patient's nasal cavities directly, and wherein said directing means is one or more louvered vents;

c) a hose having a first end and a second end adapted to be received by said first and second intake ports, and at least a third end; and d) a rotatable medication delivery port provided on said hose and positioned proximal to at least one of said intake ports; and delivering a pressurized gas into said hose wherein said [therapeutic treatment] *pressurized gas, optionally in combination with medication supplied through the rotatable medication delivery port,* is not delivered directly into the patient's nasal cavities.

12. The method according to claim 11, wherein said nasal respiratory assembly further comprises a strap and at least four loop adapters two on either side of said mask, wherein said strap has U-shaped ends adapted to be received by said at least four loop adapters for retaining said mask on the face of said patient.

13. The method according to claim 12, wherein said affixing further comprises positioning said U-shaped ends of said strap around said patient's ears.

*14. A nasal respiratory assembly for delivering a therapeutic treatment to a patient having nasal cavities, the nasal respiratory assembly comprising:*

*a) a mask comprising a top surface and a base, wherein an exhaust port is positioned on or proximate to said top surface;*

*b) at least one intake port coupled with the mask along said top surface, wherein the at least one intake port comprises an internal vent having a gas directing element comprising one or more planar surfaces or louvers within the at least one intake port, and wherein the gas directing element is configured to direct pressurized gas away from entering said patient's nasal cavities directly;*

*c) a hose configured to be received by the at least one intake port; and*

*d) at least one medication delivery port positioned upstream of the at least one intake port and configured to supply medication to the mask;*

*wherein the nasal respiratory assembly is configured to deliver said therapeutic treatment without providing a flow of pressurized gas directly into the patient's nasal cavities.*

*15. The nasal respiratory assembly of claim 14, wherein the at least one intake port comprises a first intake port and a second intake port.*

*16. The nasal respiratory assembly of claim 14, wherein the at least one medication delivery port comprises at least one rotatable medication delivery port.*

*17. The nasal respiratory assembly of claim 14, wherein:*

*the at least one intake port comprises a first intake port and a second intake port;*

*the at least one medication delivery port comprises a first medication delivery port and a second medication delivery port; and*

*the first and second delivery ports are respectively positioned on either side of the top surface of the mask, and positioned adjacent the first and second intake ports, respectively.*

*18. The nasal respiratory assembly of claim 14, wherein the one or more planar surfaces or louvers within the at least one intake port comprises a plurality of louvers within the at least one intake port.*

* * * * *